(12) United States Patent
Joo

(10) Patent No.: US 10,302,570 B2
(45) Date of Patent: May 28, 2019

(54) APPARATUS FOR PREVENTING COUNTERFEITING AND ALTERATION

(71) Applicant: NANOBRICK CO., LTD., Suwon-si (KR)

(72) Inventor: Jae Hyun Joo, Suwon-si (KR)

(73) Assignee: NANOBRICK CO., LTD., Suwon-si (KR)

( * ) Notice: Subject to any disclaimer, the term of this patent is extended or adjusted under 35 U.S.C. 154(b) by 39 days.

(21) Appl. No.: 15/284,196

(22) Filed: Oct. 3, 2016

(65) Prior Publication Data

US 2017/0024948 A1 Jan. 26, 2017

Related U.S. Application Data

(63) Continuation of application No. 14/406,527, filed as application No. PCT/KR2013/005065 on Jun. 10, 2013, now abandoned.

(30) Foreign Application Priority Data

Jun. 8, 2012 (KR) .................. 10-2012-0061695

(51) Int. Cl.
*B42D 25/369* (2014.01)
*G01N 21/66* (2006.01)
(Continued)

(52) U.S. Cl.
CPC ............. *G01N 21/66* (2013.01); *B42D 25/29* (2014.10); *B42D 25/369* (2014.10);
(Continued)

(58) Field of Classification Search
CPC ... B42D 25/369; B42D 2033/16; G01N 21/66
(Continued)

(56) References Cited

U.S. PATENT DOCUMENTS 7,295,717 B2 * 11/2007 Hersch .................... G09F 19/00
283/94
2009/0034051 A1 2/2009 Arsenault et al.
(Continued)

FOREIGN PATENT DOCUMENTS

EP 1970753 A1 9/2008
KR 10-1042263 8/2010
(Continued)

OTHER PUBLICATIONS

KR102011005392 Translation (Year: 2011).*
(Continued)

*Primary Examiner* — Kyle R Grabowski
(74) *Attorney, Agent, or Firm* — Fitch, Even, Tabin & Flannery LLP

(57) ABSTRACT

An apparatus for preventing counterfeiting and alteration according to the present invention includes a magnetic changeable substance carrier part containing a magnetic changeable substance to vary reflected or transmitted light rays as an applied magnetic field is varied; a magnetic field generation part for generating a magnetic field applied to the magnetic changeable substance; and a moveable part for varying at least one of the intensity, direction and pattern of the magnetic field applied to the magnetic changeable substance according to an externally applied stimulus so as to change the appearance of the magnetic changeable substance.

20 Claims, 15 Drawing Sheets

(a)

(b)

(51) Int. Cl.
  *G07D 7/04* (2016.01)
  *B42D 25/29* (2014.01)
  *B42D 25/378* (2014.01)
  *G01N 21/25* (2006.01)
  *G07D 7/00* (2016.01)
  *G07D 7/1205* (2016.01)
  *G09F 3/02* (2006.01)

(52) U.S. Cl.
  CPC ......... *B42D 25/378* (2014.10); *G01N 21/251* (2013.01); *G07D 7/003* (2017.05); *G07D 7/04* (2013.01); *G07D 7/1205* (2017.05); *B65D 2203/12* (2013.01); *G09F 2003/0276* (2013.01)

(58) Field of Classification Search
  USPC .............................................. 283/82, 98, 99
  See application file for complete search history.

(56) References Cited

U.S. PATENT DOCUMENTS

2011/0298880 A1  12/2011  Joo et al.

2012/0080878 A1  4/2012  Kecht et al.

FOREIGN PATENT DOCUMENTS

| | | | |
|---|---|---|---|
| KR | 10-2011-0050612 A | 5/2011 | |
| KR | 10-2011-0053929 A | 5/2011 | |
| KR | 1020110053929 A  * | 5/2011 | .............. G02F 1/15 |
| KR | 10-1119701 B1 | 3/2012 | |
| WO | 2009074284 A2 | 6/2009 | |
| WO | 2010142391 A1 | 12/2010 | |
| WO | 2010142553 A1 | 12/2010 | |
| WO | 2011-107527 A1 | 9/2011 | |

OTHER PUBLICATIONS

International Search Report dated Aug. 23, 2013 for International Application No. PCT/KR2013/005065.

Extended European Search Report dated Feb. 12, 2016 for European Patent Application No. 13800651.5.

* cited by examiner

Low ←——— Intensity of Magnetic Field ———→ High

APPARATUS FOR PREVENTING COUNTERFEITING AND ALTERATION

CROSS-REFERENCE TO A RELATED APPLICATIONS

This application is a continuation of U.S. application Ser. No. 14/406,527, filed Dec. 8, 2014, which is a national stage entry of International Application Number PCT/KR2013/005065, filed Jun. 10, 2013, which claims priority of Korean Patent Application Number 10-2012-0061695, filed Jun. 8, 2012, which are all hereby incorporated herein by reference in their entirety.

FIELD OF THE INVENTION

The present invention relates to an apparatus for preventing counterfeit and alteration. More particularly, the present invention relates to an apparatus to allow a user to determine whether an object of counterfeit and alteration prevention is counterfeited or altered, the apparatus comprising a magnetically responsive substance container to contain a magnetically responsive substance which indicates a preset color or light transmittance by changing a reflected light or a transmitted light when a magnetic field is applied thereto; a magnetic field generator to generate a magnetic field which may be applied to the magnetically responsive substance; and a movable part to perform a function of changing an indication state of the magnetically responsive substance by changing a condition of applying the magnetic field to the magnetically responsive substance (i.e., an intensity, direction or pattern of the magnetic field) in response to a given external stimulus.

BACKGROUND

Various techniques have been introduced to prevent counterfeit and alteration of high-priced goods or goods having contents of which authenticity is required. Conventionally, techniques using fine patterns, braille, hologram, RFID and the like have been mainly used to prevent counterfeit and alteration of goods. However, such conventional techniques have limitations in that it is difficult for an ordinary user to determine whether goods are counterfeited or altered, or have problems in that it costs a lot to manufacture a means for preventing counterfeit and alteration.

In this regard, the inventor has developed a method and apparatus which allow an ordinary user to easily determine whether an object of counterfeit and alteration prevention is counterfeited or altered using a substance of which color or light transmittance is changed as a magnetic field is applied thereto.

SUMMARY OF THE INVENTION

One object of the invention is to solve all the above-described problems.

Another object of the invention is to provide an apparatus for preventing counterfeit and alteration, which may use a magnetically responsive substance that changes a reflected or transmitted light to indicate a preset color or light transmittance when a magnetic field is applied thereto, and may change an indication state of the magnetically responsive substance by changing a condition of applying the magnetic field to the magnetically responsive substance (i.e., an intensity, direction or pattern of the magnetic field) in response to a given external stimulus.

A counterfeit and alteration prevention apparatus according to the invention comprises a magnetically responsive substance container to contain a magnetically responsive substance in which a reflected light or a transmitted light is changed when a magnetic field applied thereto is changed; a magnetic field generator to generate a magnetic field capable of being applied to the magnetically responsive substance; and a movable part to perform a function of changing an indication state of the magnetically responsive substance by changing at least one of an intensity, a direction and a pattern of the magnetic field applied to the magnetically responsive substance in response to a given external stimulus.

The movable part may be moved, rotated or deformed in response to the given external stimulus to change at least one of the intensity, direction and pattern of the magnetic field generated by the magnetic field generator and applied to the magnetically responsive substance.

The movable part may be moved, rotated or deformed in response to the given external stimulus to move the magnetically responsive substance container to a region where the magnetic field generated by the magnetic field generator is applied.

The movable part may be moved, rotated or deformed in response to the given external stimulus to move the magnetically responsive substance contained in the magnetically responsive substance container to a region where the magnetic field generated by the magnetic field generator is applied.

The movable part may be moved, rotated or deformed in response to the given external stimulus to move the magnetic field generator to a region where a magnetic field is capable of being applied to the magnetically responsive substance.

At least one of the magnetically responsive substance container, the magnetic field generator and the movable part may be irreversibly fractured by the external stimulus. When at least one of the magnetically responsive substance container, the magnetic field generator and the movable part is irreversibly fractured, the reflected light and the transmitted light of the magnetically responsive substance may not be changed even if the magnetic field is applied.

The magnetically responsive substance may be set to reflect light having a preset wavelength or transmit light at a preset transmittance as the magnetic field is applied thereto.

At least one of the magnetically responsive substance container, the magnetic field generator and the movable part may be configured in the form of at least one of a container plug, a tag, a card, a film, and a sticker.

The magnetically responsive substance may include a solution in which magnetic particles are dispersed, and intervals between or positions of the magnetic particles are changed according to a change of the magnetic field applied thereto.

The magnetically responsive substance may include at least one of a fluorescent material, a phosphorescent material, a quantum dot material, a temperature indicating material, and an optically variable pigment (OVP) material.

The magnetically responsive substance may be encapsulated into a capsule made of a light-transmissive material.

The counterfeit and alteration prevention apparatus may further comprise an additional counterfeit and alteration prevention means using at least one of hologram, radio frequency identification (RFID) and biometric information recognition.

According to the invention, an ordinary user may easily determine whether an object of counterfeit and alteration prevention is counterfeited or altered by merely operating the movable part and observing an indication state of the magnetically responsive substance with the naked eye.

DETAILED DESCRIPTION OF THE PREFERRED EMBODIMENTS

Figure 1:
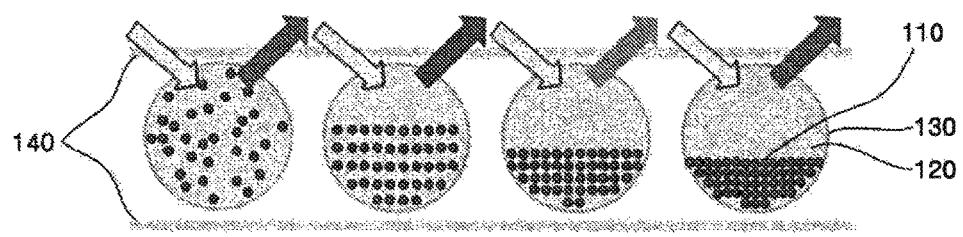
FIG. 1 illustratively shows a principle of adjusting a wavelength of light reflected from a magnetically responsive substance according to one embodiment of the invention.

In the following detailed description of the present invention, references are made to the accompanying drawings that show, by way of illustration, specific embodiments in which the invention may be practiced. These embodiments are described in sufficient detail to enable those skilled in the art to practice the invention. It shall be understood that the various embodiments of the invention, although different from each other, are not necessarily mutually exclusive. For example, specific shapes, structures and characteristics described herein may be implemented as modified from one embodiment to another without departing from the spirit and scope of the invention. In addition, it shall be understood that the locations or arrangements of individual elements within each of the disclosed embodiments may also be modified without departing from the spirit and scope of the invention. Accordingly, the following detailed description is not to be taken in a limiting sense, and the scope of the invention, if properly described, is limited only by the appended claims together with all equivalents thereof. In the drawings, like reference numerals refer to the same or similar functions throughout the several views.

Hereinafter, the configurations of the present invention will be described in detail with reference to the accompanying drawings so that those skilled in the art to which the invention pertains may easily implement the invention.

Configuration of a Magnetically Responsive Substance

According to one embodiment of the invention, particles included in a magnetically responsive substance may be magnetic so that they are rotatable or movable when subjected to a magnetic force by a magnetic field. For example, the particles may include a magnetic material such as nickel (Ni), iron (Fe) and cobalt (Co).

Further, according to one embodiment of the invention, the particles may include a material which becomes magnetic (i.e. becomes magnetized) when a magnetic field is applied thereto. In particular, according to one embodiment of the invention, a superparamagnetic material, which is magnetized when an external magnetic field is applied thereto but does not have a remanent magnetization when no external magnetic field is applied thereto, may be employed to prevent magnetic particles from agglomerating together when no magnetic field is externally applied thereto.

Furthermore, according to one embodiment of the invention, the surface of the particles may be coated with charges with the same polarity so that the particles may be well dispersed in a solvent without being flocculated. In addition, in order to prevent the particles from being precipitated in the solvent, a material having a specific gravity different from that of the particles may be coated on the surface of the particles, or may be mixed with the solvent.

Further, according to one embodiment of the invention, the particles may be configured to reflect light having a specific wavelength, i.e., to have a specific color. More specifically, the particles according to the invention may have a specific color by adjusting an oxidation state thereof or by coating an inorganic pigment, dye or the like thereon. For example, Zn, Pb, Ti, Cd, Fe, As, Co, Mg, Al or the like including a chromophoric group may be used as the inorganic pigment coated on the particles according to the invention, in the form of oxide, emulsion or lactate, and a fluorescent dye, acidic dye, basic dye, mordant dye, sulfide dye, vat dye, dispersed dye, reactive dye or the like may be used as the dye coated on the particles according to the invention. In addition, according to one embodiment of the invention, the particles included in the magnetically responsive substance may consist of a fluorescent material, a phosphorescent material, a quantum dot material, a temperature indicating material, an optically variable pigment (OVP) material, or the like.

Furthermore, according to one embodiment of the invention, silica, polymer, monomer or the like may be coated on the surface of the particles so that the particles may have high dispersibility and stability in the solvent.

Meanwhile, the diameter of the particles according to the invention may range from tens of nanometers to tens of micrometers, but not limited thereto.

Next, the configuration of a solvent included in the magnetically responsive substance will be described in detail.

According to one embodiment of the invention, the solvent may consist of a material having a specific gravity similar to that of the particles so that the particles may be evenly dispersed therein, or a material suitable for allowing the particles to be stably dispersed in the solvent. For example, the material may include halogen carbon oil, dimethyl silicon oil or the like, which has a low dielectric constant.

Further, according to one embodiment of the invention, the solvent may be configured to reflect light having a specific wavelength, i.e., to have a specific color. More specifically, the solvent according to the invention may include a material having an inorganic pigment or a dye, or a material having a structural color based on photonic crystals.

Furthermore, according to one embodiment of the invention, by allowing magnetic particles to be evenly dispersed in a fat-soluble solvent, it is possible to prevent the particles from agglomerating together or adhering to an inner wall of a capsule in an encapsulation process.

However, the configurations of the particles and the solvent according to the invention are not limited to those described above, and may be appropriately modified as long as the objects of the invention may be achieved.

Next, it will be described in detail how the particles and solvent included in the magnetically responsive substance according to the invention are encapsulated or partitioned.

According to one embodiment of the invention, the particles may be encapsulated into a plurality of capsules made of a light-transmissive material as dispersed in the solvent. According to one embodiment of the invention, occurrence of direct interference such as intermixing between different capsules may be prevented by encapsulating the particles and solvent, so that the particles included in the magnetically responsive substance may be independently controlled for each capsule. As a result, light transmission may be adjusted in more various patterns and light transmittance control characteristics may be improved.

For example, gelatin, acacia, melamine, urea, protein, polysaccharide or the like may be used as a material constituting the capsules according to one embodiment of the invention, and a material for fixing the capsules (i.e., a binder) may be used. However, the configuration of the capsules according to the invention is not necessarily limited to the above-described examples, and any material may be used as the material for the capsules according to the invention as long as it is light-transmissive, physically strong, elastic but not hard, non-porous, and resistant to external heat and pressure.

In addition, according to one embodiment of the invention, the particles may be partitioned as dispersed in the solvent. According to one embodiment of the invention, direct interference such as intermixing between different cells divided by partitions may be prevented, and thus the particles included in a magnetically responsive substance container to be described later may be independently controlled for each capsule.

FIG. 1 illustratively shows a principle of adjusting a wavelength of light reflected from a magnetically responsive substance according to one embodiment of the invention.

According to one embodiment of the invention, when a magnetic field is applied to a plurality of particles 110 which are magnetic and have charges on the surface thereof, a magnetic attractive force acts on the particles 110 in a predetermined direction due to the magnetism of each of the particles 110. Thus, a distance between the particles 110 gathered to one side is reduced, while a magnetic repulsive force caused by Coulomb's law (when the particles have the same surface charges) or a physical repulsive force caused by steric hindrance effects (when a hydrodynamic size of the particles is large due to a detecting functional group attached to the surface of the particles) acts between the particles 110. Accordingly, an interval of the particles 110 may be determined based on a relative strength between the attractive force caused by the magnetic field and the repulsive force between the particles caused by the charges. As a result, the particles 110 arranged at a predetermined interval may function as photonic crystals. That is, according to Bragg's law, a wavelength of light reflected from the particles 110 is determined by the interval of the particles 110, and thus the wavelength of the light reflected from the particles 110 may be adjusted by controlling the interval of the particles 110.

Here, a wavelength pattern of the reflected light may be varied depending on factors such as an intensity and direction of the magnetic field, a size and mass of the particles, refractive indices of the particles and the solvent, a magnetization value of the particles, an amount of the charges of the particles, and a concentration of the particles dispersed in the solvent.

Referring to FIG. 1, when no magnetic field is applied, the particles 110 may be irregularly arranged in a capsule 130. In this case, the particles 110 do not exhibit any specific color. Next, when a predetermined magnetic field is applied, an attractive force caused by the magnetic field and a repulsive force between the particles 110 caused by the charges may be balanced so that the particles 110 may be regularly arranged at a predetermined interval. As a result, the interval of the plurality of particles 110 may be controlled so that light having a specific wavelength may be reflected therefrom. In addition, when the intensity of the magnetic field applied to the particles 110 is increased, the attractive force caused by the magnetic field is also increased so that the interval of the particles 110 is narrowed and thus the wavelength of the light reflected from the particles 110 is shortened. That is, according to one embodiment of the invention, the wavelength of the light reflected from the particles 110 may be adjusted by adjusting the intensity of the magnetic field applied to the particles 110. As the intensity of the magnetic field is further increased, the wavelength of the light reflected from the particles may go beyond a visible light range and fall within an ultraviolet range. Then, the particles may transmit visible rays without reflecting them, and in this case, the light transmittance may be increased.

Meanwhile, according to one embodiment of the invention, the magnetically responsive substance consisting of the particles 110 and solvent 120 may be encapsulated into the capsule 130 made of a light-transmissive material, as shown in FIG. 1.

Figure 2:
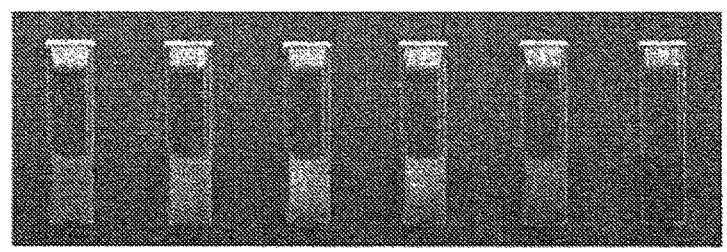
FIG. 2 shows a result of photographing color changes of a magnetically responsive substance appearing when various intensities of magnetic fields are applied thereto according to one embodiment of the invention.

FIG. 2 shows a result of photographing color changes of a magnetically responsive substance appearing when various intensities of magnetic fields are applied thereto according to one embodiment of the invention.

Referring to FIG. 2, it can be seen that as the intensities of the applied magnetic fields are adjusted, the light reflected from the particles may be adjusted to have any color ranging from red to green and to violet, i.e., in the entire visible light wavelength range.

Figure 3:
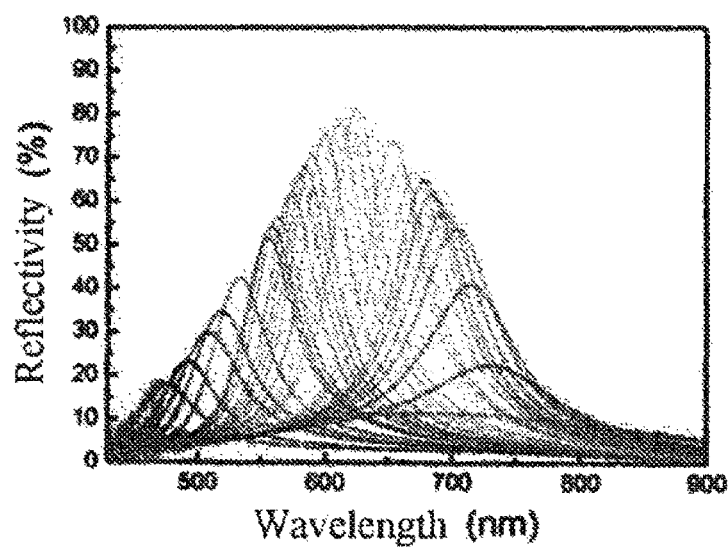
FIG. 3 shows a graph representing measured wavelengths of light reflected from a magnetically responsive substance with regard to intensities of a magnetic field according to one embodiment of the invention.

FIG. 3 shows a graph representing measured wavelengths of light reflected from a magnetically responsive substance with regard to intensities of a magnetic field according to one embodiment of the invention. It can be seen that as the intensity of the applied magnetic field is increased, the light is gradually changed from a reddish light having a long wavelength to a bluish light having a short wavelength.

Figure 4:
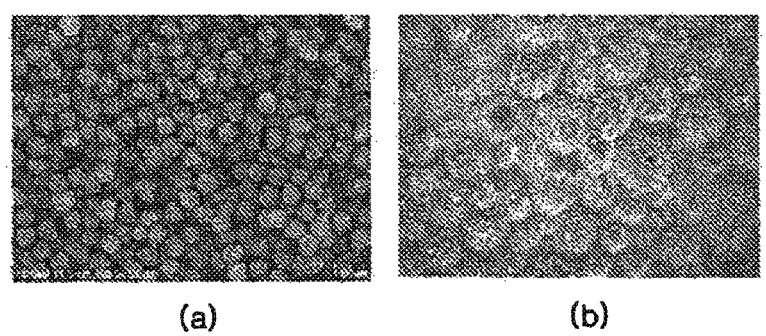
FIG. 4 shows an SEM photograph (a) of magnetic particles constituting a magnetically responsive substance according to one embodiment of the invention, and a photograph (b) of the magnetically responsive substance according to one embodiment of the invention being encapsulated into a capsule made of a light-transmissive material and then subjected to a magnetic field so that a greenish light is reflected therefrom.

(a) of FIG. 4 shows an SEM photograph of magnetic particles constituting a magnetically responsive substance according to one embodiment of the invention. In (a) of FIG. 4, superparamagnetic $Fe_3O_4$ particles ranging from 50 nm to 300 nm are used as the magnetic particles.

(b) of FIG. 4 shows a photograph of the magnetically responsive substance according to one embodiment of the invention being encapsulated into a capsule made of a light-transmissive material and then subjected to a magnetic field so that a greenish light is reflected therefrom. Referring to (b) of FIG. 4, it can be seen that the particles within the capsule are regularly arranged at a specific interval according to the magnetic field, and thus a greenish light in a specific wavelength range is mainly reflected.

Figure 5:
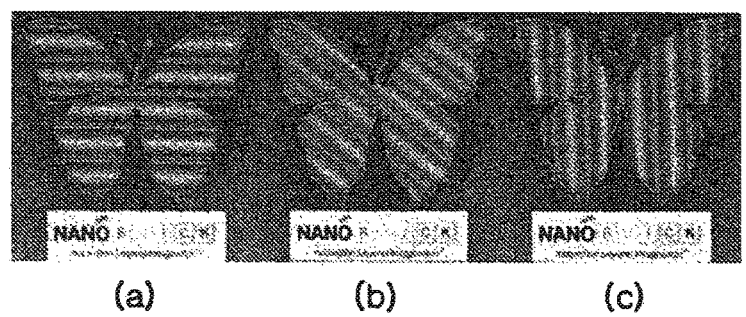
FIG. 5 shows photographs taken by observing changes in color and pattern of a magnetically responsive substance according to one embodiment of the invention, wherein the magnetically responsive substance is formed with a butterfly pattern thereon and positioned above a magnet in which magnetic poles for generating different intensities of magnetic fields are alternately formed in a stripe shape, and then the magnet is rotated.

FIG. 5 shows photographs taken by observing changes in color and pattern of a magnetically responsive substance according to one embodiment of the invention, wherein the magnetically responsive substance is formed with a butterfly pattern thereon and positioned above a magnet in which magnetic poles for generating different intensities of magnetic fields are alternately formed in a stripe shape, and then the magnet is rotated.

Meanwhile, according to one embodiment of the invention, the magnetically responsive substance may include particles having magnetophoretic properties.

Specifically, when a magnetic field is applied to the magnetically responsive substance according to one embodiment of the invention, the magnetic particles may be moved in the same direction as the magnetic field or in the opposite direction. As a result, an inherent color of the particles or the solvent may be indicated.

Meanwhile, according to one embodiment of the invention, the magnetically responsive substance may include a material having a light transmittance which may be changed as a magnetic field is applied thereto.

Figure 6:
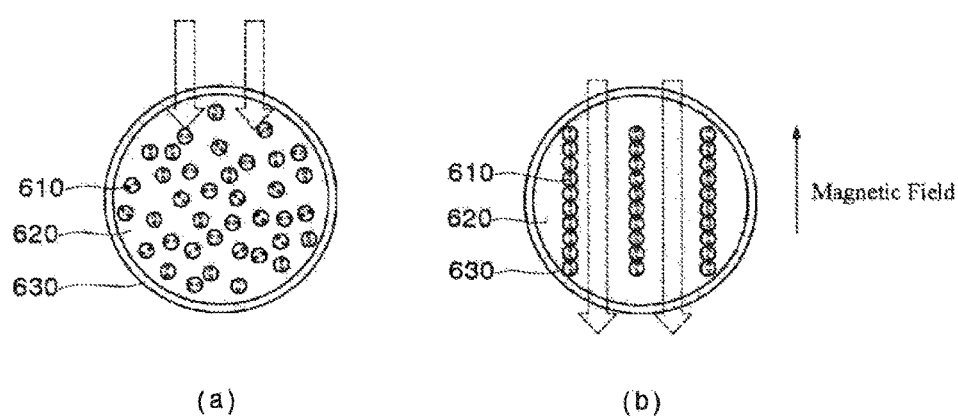
FIG. 6 illustratively shows how light transmittance of a magnetically responsive substance is changed according to one embodiment of the invention.

FIG. 6 illustratively shows how light transmittance of a magnetically responsive substance is changed according to one embodiment of the invention.

Referring to FIG. 6, the magnetically responsive substance container according to one embodiment of the invention may contain a plurality of magnetic particles 610, a solvent 620 and a capsule 630, and the plurality of magnetic particles 610 may be contained in the capsule 630 as dispersed in the solvent 620.

First, referring to (a) of FIG. 6, when no magnetic field is applied to the magnetically responsive substance container, the plurality of magnetic particles 610 may be irregularly dispersed in the capsule 630. In this case, the transmittance of light incident on the magnetically responsive substance is not particularly controlled. That is, the light incident on the magnetically responsive substance is scattered or reflected by the plurality of irregularly dispersed particles 110, and thus the light transmittance becomes relatively low.

Next, referring to (b) of FIG. 6, when a magnetic field is applied to the magnetically responsive substance, the plurality of magnetic particles 110 within the capsule 130 may be arranged in a direction parallel to that of the magnetic field, and thus the transmittance of the light incident on the magnetically responsive substance container may be controlled.

Specifically, when a magnetic field is applied to the magnetically responsive substance according to one embodiment of the invention, each of the plurality of the particles 110, which are originally magnetic or magnetized by the magnetic field, may be rotated or moved such that a direction from S-pole to N-pole of the plurality of particles 110 is the same as that of the magnetic field. The N-pole and S-pole of each of the rotated or moved particles 110 become closer to the S-pole and N-pole of the nearby particles 110, respectively, so that a magnetic attractive or repulsive force is generated between the plurality of particles 110, and thus the plurality of particles 110 may be regularly aligned in a direction parallel to that of the magnetic field. That is, the plurality of particles 110 may be regularly aligned in a direction parallel to that of the vertically applied magnetic field. In this case, the light incident on the magnetically responsive substance is less scattered or reflected by the plurality of particles 110, and thus the light transmittance becomes relatively high.

Configuration of a Counterfeit and Alteration Prevention Apparatus

According to one embodiment of the invention, a counterfeit and alteration prevention apparatus may comprise a magnetically responsive substance container, a magnetic field generator, and a movable part.

First, according to one embodiment of the invention, the magnetically responsive substance container may contain a magnetically responsive substance in which a reflected light or a transmitted light is changed when a magnetic field applied thereto is changed. Specifically, the magnetically responsive substance contained in the magnetically responsive substance container may be configured (or set) to reflect light having a specific wavelength or to indicate a specific light transmittance when a magnetic field having a specific intensity and direction is applied thereto. As will be described below, the magnetically responsive substance may be utilized as a visual indicator when an ordinary user determines with the naked eye whether an object of counterfeit and alteration prevention is authentic or not.

Further, according to one embodiment of the invention, the magnetically responsive substance container may be configured to be fractured when the object of counterfeit and alteration prevention is opened. Thus, after the object of counterfeit and alteration prevention is opened, the reflected or transmitted light of the magnetically responsive substance may not be changed even if a magnetic field is applied to the magnetically responsive substance, and thus the magnetically responsive substance may not reflect light having a preset wavelength or indicate a preset light transmittance.

Next, according to one embodiment of the invention, the magnetic field generator may perform a function of generating a magnetic field which may be applied to the magnetically responsive substance. According to one embodiment of the invention, the magnetic field generator may be formed in a preset pattern so that the magnetically responsive substance may indicate a preset color or light transmittance according to a predetermined pattern. For example, the magnetic field generator may generate a magnetic field having a predetermined intensity and direction along a shape such as a logo, character, bar code and figure, which serves as a reference in determining whether an object of counterfeit and alteration prevention is counterfeited or altered.

Next, according to one embodiment of the invention, the movable part may perform a function of changing an indication state of the magnetically responsive substance by changing a condition of applying a magnetic field to the magnetically responsive substance (i.e., an intensity, direction or pattern of the magnetic field) in response to a given external stimulus. Here, the external stimulus given to the movable part may be induced by a user who desires to determine whether an object of counterfeit and alteration prevention is authentic or not, a user who desires to open the object of counterfeit and alteration prevention, a user who desires to use the object of counterfeit and alteration prevention, or the like.

Specifically, the movable part according to one embodiment of the invention may be moved, rotated or bent in response to the given external stimulus to perform a function of moving the magnetically responsive substance container to a region where the magnetic field generated by the magnetic field generator is applied.

Further, the movable part according to one embodiment of the invention may be moved, rotated, bent, or fractured in response to the given external stimulus to perform a function of moving the magnetically responsive substance contained in the magnetically responsive substance container to a region where the magnetic field generated by the magnetic field generator is applied.

Furthermore, the movable part according to one embodiment of the invention may be moved, rotated or bent in response to the given external stimulus to perform a function of moving the magnetic field generator to a region where the magnetic field may be applied to the magnetically responsive substance.

Hereinafter, various embodiments of the counterfeit and alteration prevention apparatus according to the invention will be described in detail with reference to the accompanying drawings.

FIGS. 7 to 21 illustratively show the configurations of counterfeit and alteration prevention apparatuses according to one embodiment of the invention.

Figure 7:
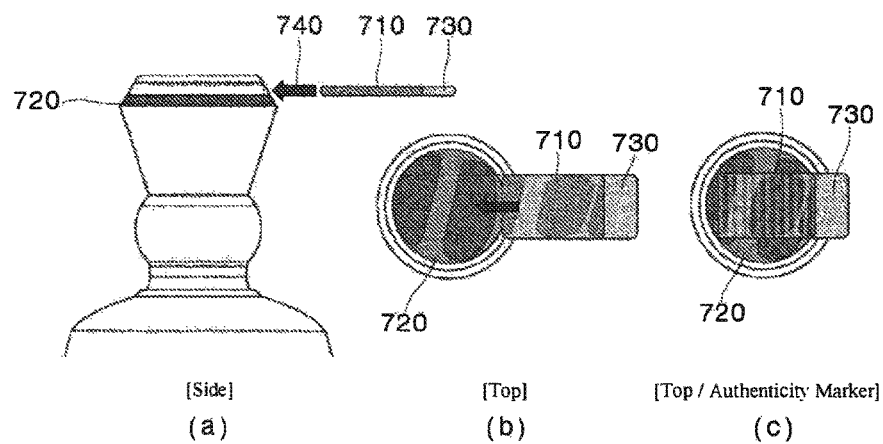
FIGS. 7 to 21 illustratively show the configurations of counterfeit and alteration prevention apparatuses according to one embodiment of the invention.

First, referring to FIG. 7, a magnetically responsive substance container containing a magnetically responsive substance 710 may be coated on the top of a bar-shaped movable part 730. When the magnetically responsive substance 710 is positioned in the vicinity of a magnetic field generator 720 as the movable part 730 is slid along a route provided on a cap of an object of counterfeit and alteration prevention by an external stimulus 740 such as a user's operation, a magnetic field is applied to the magnetically responsive substance 710 so that a preset color may be indicated along a preset pattern (e.g., a logo, character, bar code, or figure) or a preset light transmittance may be indicated along the preset pattern (see (c) of FIG. 7).

Figure 8:
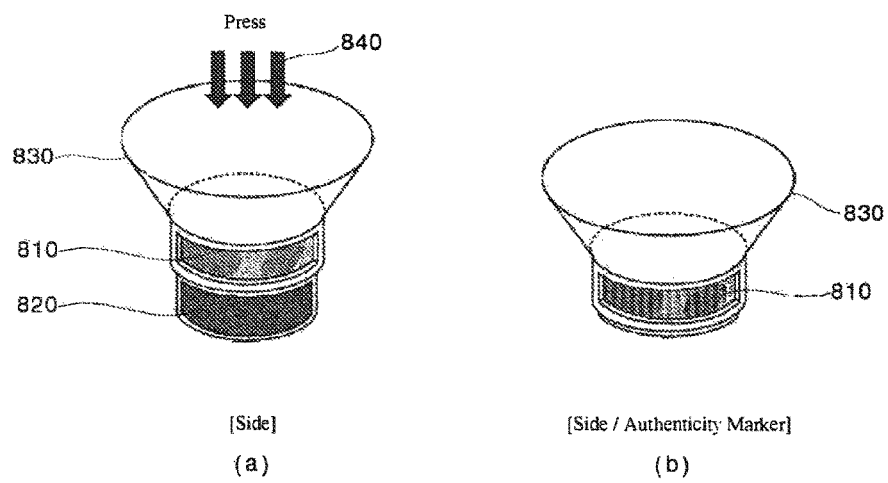

Next, referring to FIG. 8, a magnetically responsive substance container containing a magnetically responsive substance 810 may be disposed along the circumference of a ring-shaped movable part 830. When the magnetically responsive substance 810 is positioned in the vicinity of a magnetic field generator 820 as the movable part 830 is moved downward along a route provided on a cap of an object of counterfeit and alteration prevention by an external stimulus 840 such as a user's operation, a magnetic field is applied to the magnetically responsive substance 810 so that a preset color may be indicated along a preset pattern (e.g., a logo, character, bar code, or figure) or a preset light transmittance may be indicated along the preset pattern (see (b) of FIG. 8).

Figure 9:
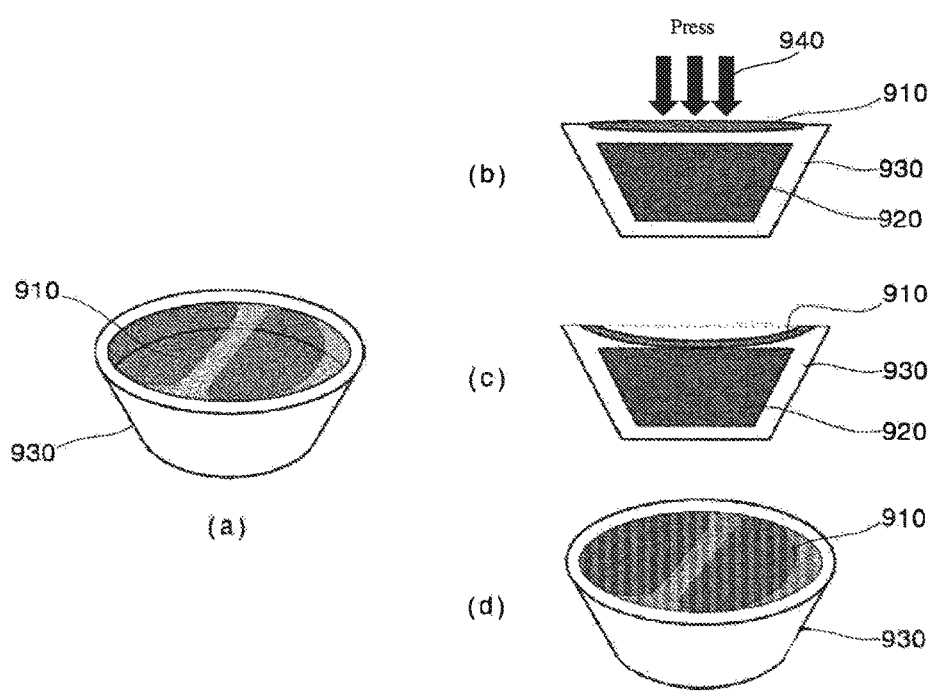
Figure 10:
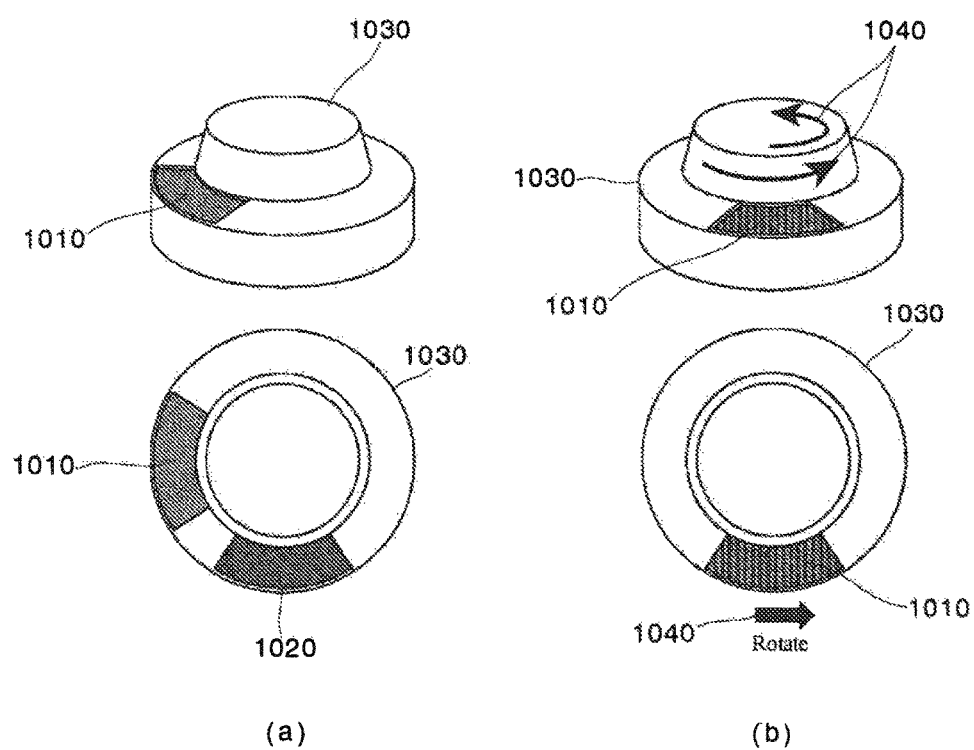
Figure 11:
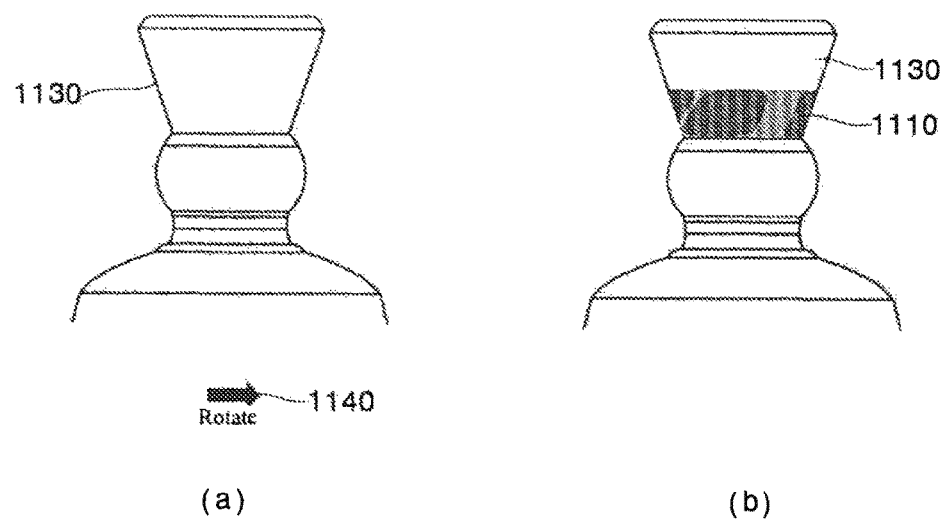
Figure 12:
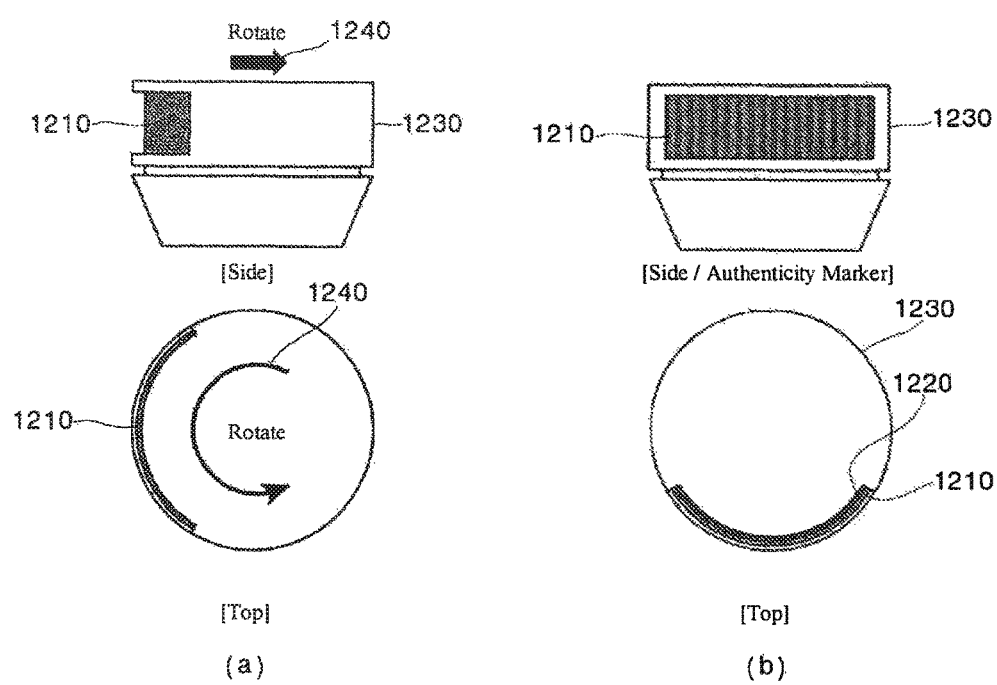
Figure 13:
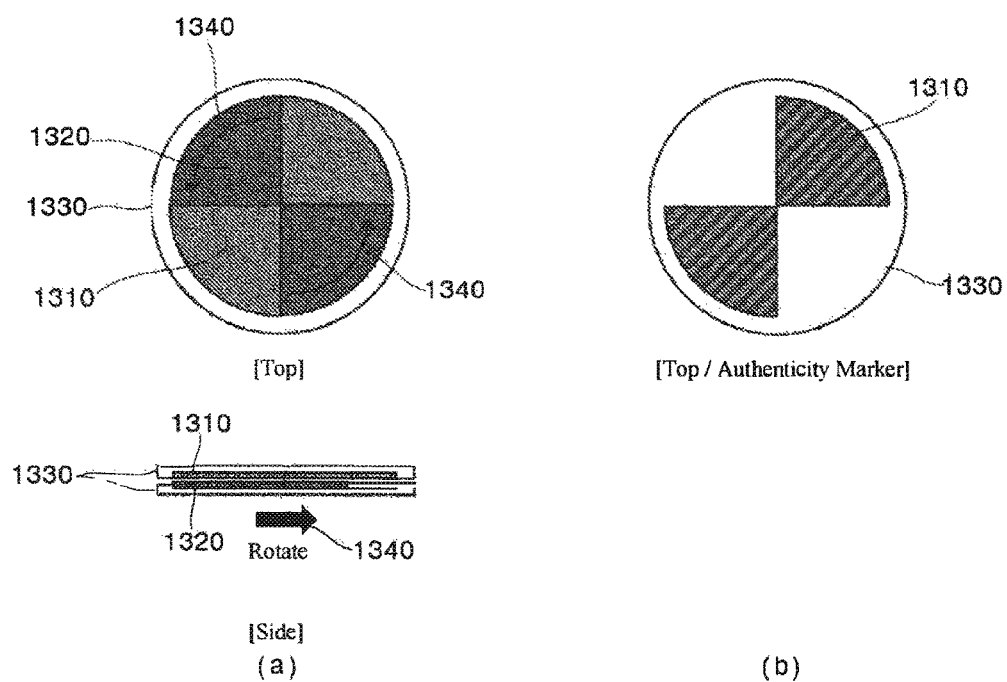

Next, referring to FIG. 9, a magnetically responsive substance container containing a magnetically responsive substance 910 may be disposed on the top of a ring-shaped movable part 930. When the magnetically responsive substance 910 is positioned in the vicinity of a magnetic field generator 920 as the top of the movable part 930 is bent downward by an external stimulus 940 such as a user's operation, a magnetic field is applied to the magnetically responsive substance 910 so that a preset color may be indicated along a preset pattern (e.g., a logo, character, bar code, or figure) or a preset light transmittance may be indicated along the preset pattern (see (d) of FIG. 9).

Next, referring to FIGS. 10 to 13, a magnetically responsive substance container containing a magnetically responsive substance 1010, 1110, 1210, 1310 may be disposed along the circumference of a ring-shaped movable part 1030, 1130, 1230, 1330. When the magnetically responsive substance 1010, 1110, 1210, 1310 is positioned in the vicinity of a magnetic field generator 1020, 1120, 1220, 1320 as the movable part 1030, 1130, 1230, 1330 or the magnetic field generator 1020, 1120, 1230, 1330 is rotated along a route provided on a cap of an object of counterfeit and alteration prevention by an external stimulus 1040, 1140, 1240, 1340 such as a user's operation, a magnetic field is applied to the magnetically responsive substance 1010, 1110, 1210, 1310 so that a preset color may be indicated along a preset pattern (e.g., a logo, character, bar code, or figure) or a preset light transmittance may be indicated along the preset pattern (see (d) of FIGS. 10, 11, 12 and 13).

Figure 14:
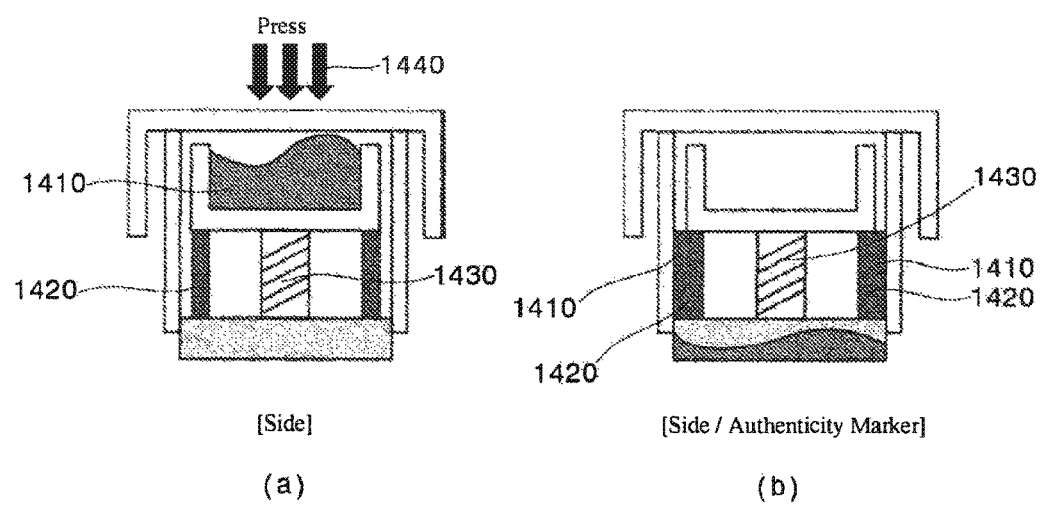

Next, referring to FIG. 14, a liquid magnetically responsive substance 1410 may be disposed on the top of a movable part 1430 made of an elastic material such as a spring. When the magnetically responsive substance 1410 flows downward to be positioned in the vicinity of a magnetic field generator 1420 as the movable part 1430 is pressed downward by an external stimulus 1440 such as a user's operation, a magnetic field is applied to the magnetically responsive substance 1410 so that a preset color may be indicated along a preset pattern (e.g., a logo, character, bar code, or figure) or a preset light transmittance may be indicated along the preset pattern (see (b) of FIG. 14).

Figure 15:
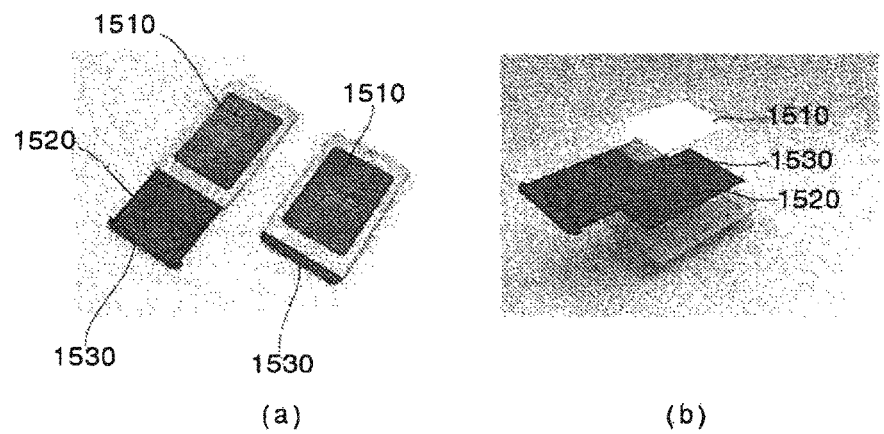

Next, referring to FIG. 15, a magnetic field generator 1520 may be disposed on the top or bottom of a bar-shaped movable part 1530. When a magnetically responsive substance 1510 is positioned in the vicinity of the magnetic field generator 1520 as the movable part 1530 is slid into a space below a surface formed with the magnetically responsive substance 1510 by an external stimulus such as a user's operation, a magnetic field is applied to the magnetically responsive substance 1510 so that a preset color may be indicated along a preset pattern (e.g., a logo, character, bar code, or figure) or a preset light transmittance may be indicated along the preset pattern (see (b) of FIG. 15).

Figure 16:
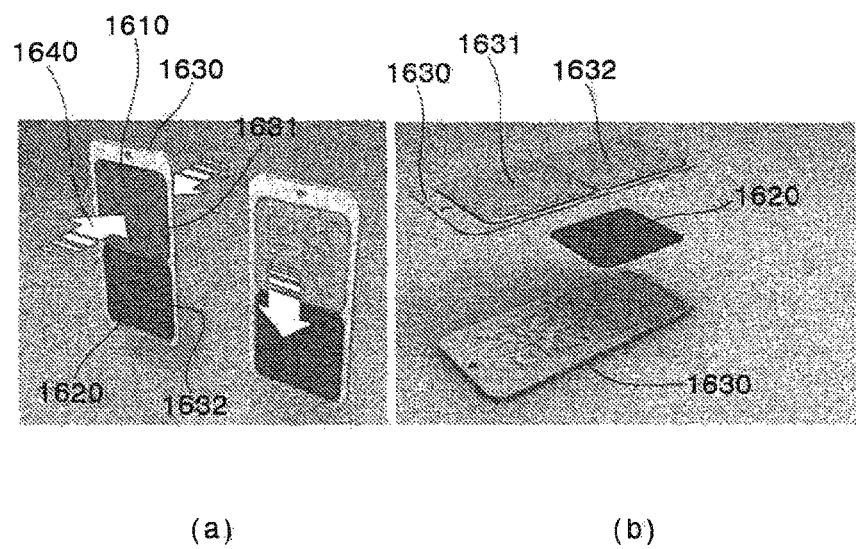

Next, referring to FIG. 16, a liquid magnetically responsive substance 1610 may be injected into a first space 1631 within a movable part 1630 and a magnetic field generator 1620 may be disposed to generate a magnetic field for a second space 1632 within the movable part 1630. When the magnetically responsive substance 1610 is positioned in the vicinity of the magnetic field generator 1620 as the first space of the movable part 1630 is pressed by an external stimulus 1640 such as a user's operation so that the magnetically responsive substance 1610 is moved from the first space 1631 to the second space 1632, a magnetic field is applied to the magnetically responsive substance 1610 so that a preset color may be indicated along a preset pattern (e.g., a logo, character, bar code, or figure) or a preset light transmittance may be indicated along the preset pattern (see (b) of FIG. 16).

Figure 17:
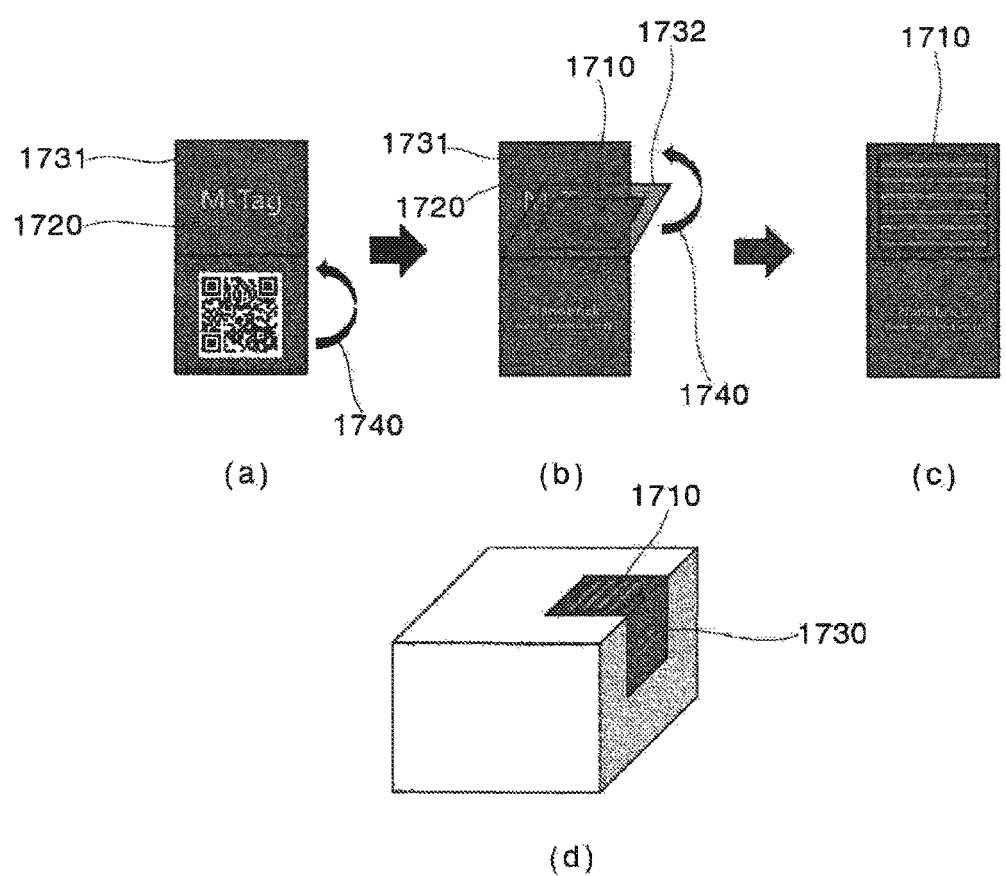

Next, referring to FIG. 17, a movable part 1730 may be configured in the form of a film type sticker attachable to an object of counterfeit and alteration prevention, and may comprise a magnetically responsive substance 1710 and a magnetic field generator 1720. Specifically, the magnetically responsive substance 1710 may be disposed in a first portion 1731 which may be moved by an external stimulus without adhering to the object of counterfeit and alteration prevention, and the magnetic field generator 1720 may be disposed in a second portion 1732 which adheres to the object of counterfeit and alteration prevention. Accordingly, when the magnetically responsive substance 1710 is positioned in the vicinity of the magnetic field generator 1720 as the first portion 1731 of the movable part 1730 is folded toward the second portion 1732 by an external stimulus 1740 such as a user's operation, a magnetic field is applied to the magnetically responsive substance 1710 so that a preset color may be indicated along a preset pattern (e.g., a logo, character, bar code, or figure) or a preset light transmittance may be indicated along the preset pattern (see (c) of FIG. 17). In addition, referring to FIG. 17, the movable part 1730 according to one embodiment of the invention may be configured such that the first portion 1731 in which the magnetically responsive substance 1710 is disposed may be fractured when the object of counterfeit and alteration prevention is opened. After the first portion 1731 is fractured, the magnetically responsive substance 1710 may not indicate the preset color or light transmittance even if a magnetic field is applied to the magnetically responsive substance 1710.

Figure 18:
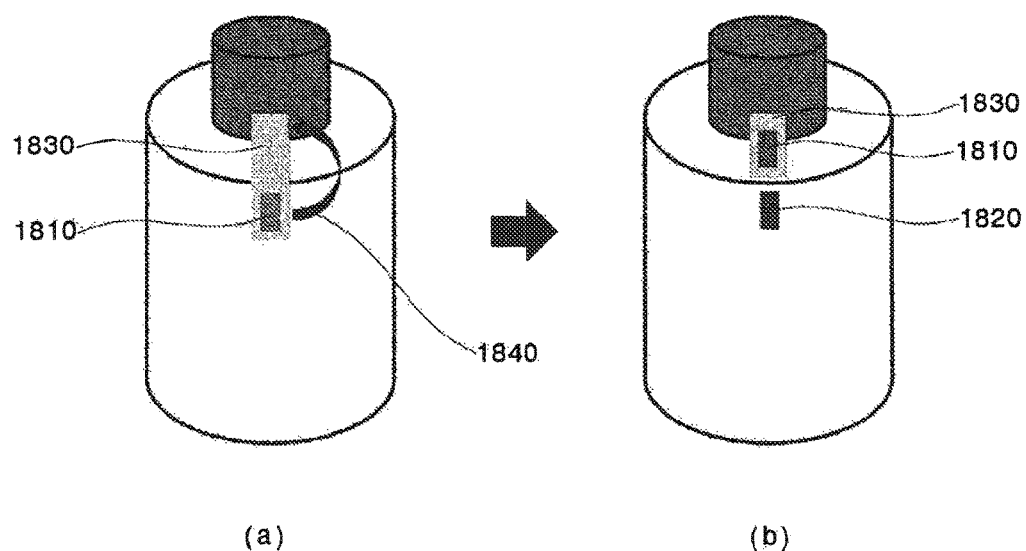

Next, referring to FIG. 18, a movable part 1830 may be configured in the form of a film type sticker attachable to both of a cap and a body of an object of counterfeit and alteration prevention, and both of a magnetically responsive substance 1810 and a magnetic field generator 1820 may be disposed in a portion contacting the object of counterfeit and alteration prevention. The magnetically responsive substance 1810 may be disposed such that a preset color may be indicated along a preset pattern (e.g., a logo, character, bar code, or figure) or a preset light transmittance may be indicated along the preset pattern as a magnetic field generated from the magnetic field generator 1820 is applied thereto. In addition, the movable part 1830 according to one embodiment of the invention may be configured such that the portion in which the magnetically responsive substance 1810 is disposed may be fractured when the object of counterfeit and alteration prevention is opened. After the portion is fractured, the magnetically responsive substance 1810 may not indicate the preset color or light transmittance even if a magnetic field is applied to the magnetically responsive substance 1810.

Figure 19:
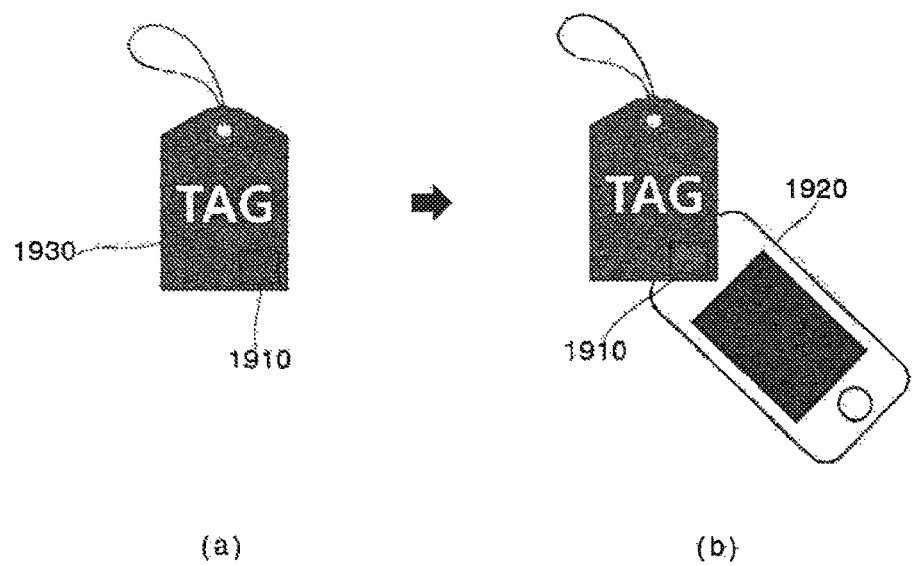
Figure 20:
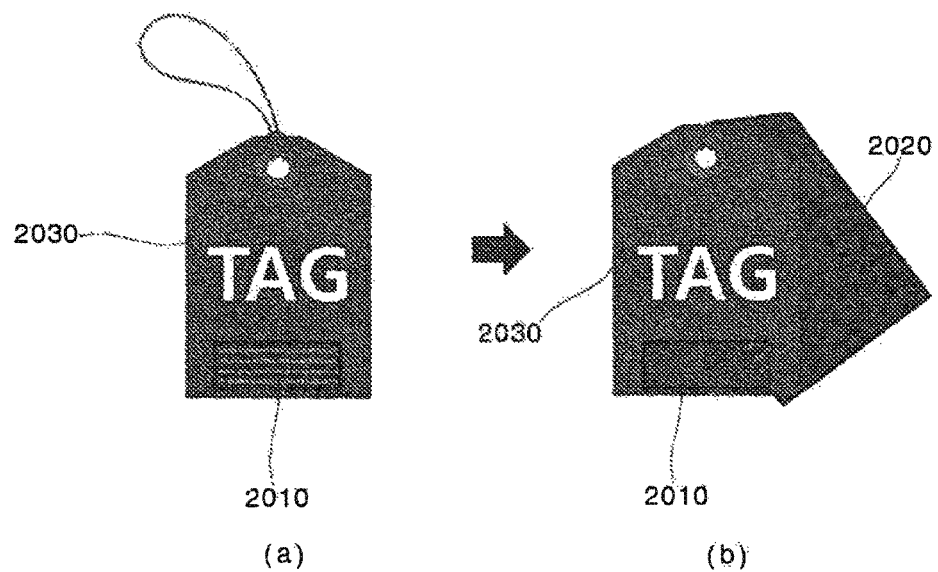
Figure 21:
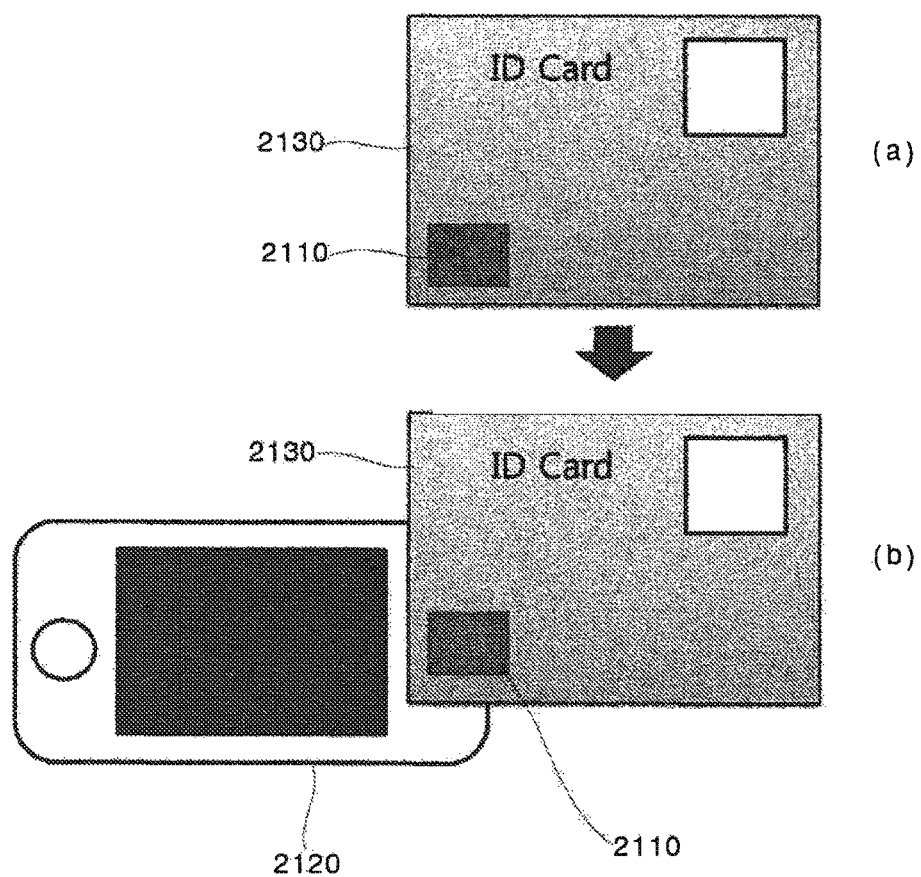

Next, referring to FIGS. 19 to 21, a movable part 1930, 2030, 2130 may be configured in the form of a tag, card or the like in at least a portion of which a magnetically responsive substance 1910, 2010, 2110 is disposed. Accordingly, when the movable part 1930, 2030, 2130 approaches an object including a magnetic field generator 1920, 2020, 2120 (e.g., a tag or a mobile phone), a preset color may be indicated along a preset pattern (e.g., a logo, character, bar code, or figure) or a preset light transmittance may be indicated along the preset pattern as a magnetic field generated from the magnetic field generator 1920, 2020, 2120 is applied to the magnetically responsive substance 1910, 2010, 2110 (see (b) of FIGS. 19, 20 and 21).

Meanwhile, the counterfeit and alteration prevention apparatus according to the invention may further comprise an additional counterfeit and alteration prevention means using at least one of hologram, radio frequency identification (RFID) and biometric information recognition. As a result, counterfeiting and alteration of an object may be prevented more effectively.

Although the present invention has been described in terms of specific items such as detailed elements as well as the limited embodiments and the drawings, they are only provided to help more general understanding of the invention, and the present invention is not limited to the above embodiments. It will be appreciated by those skilled in the art to which the present invention pertains that various modifications and changes can be made from the above description.

Accordingly, the spirit of the present invention shall not be limited to the above-described embodiments, and the entire scope of the appended claims and their equivalents will fall within the spirit and scope of the invention.

What is claimed is:

1. A counterfeit and alteration prevention apparatus comprising:
    a magnetically responsive substance container to contain a magnetically responsive substance in which a reflected light or a transmitted light is changed when a magnetic field applied thereto is changed;
    a magnetic field generator to generate a magnetic field capable of being applied to the magnetically responsive substance; and
    a movable part to perform a function of changing an indication state of the magnetically responsive substance, wherein the movable part includes the magnetically responsive substance container, and
    wherein the movable part is configured to move the magnetically responsive substance container to a region where the magnetic field generated by the magnetic field generator is applied, and to change at least one of an intensity, a direction and a pattern of the magnetic field applied to the magnetically responsive substance such that the magnetically responsive substance container displays the indication state of the magnetically responsive substance,
    wherein the indication state of the magnetically responsive substance is specific to the magnetic field generator based on the magnetic field generated by the magnetic field generator,
    wherein the magnetically responsive substance container is disposed along a circumference of the movable part,
    wherein the movable part or the magnetic field generator is configured to allow the movable part or the magnetic field generator to be rotated along a route provided on a cap to cause the magnetically responsive substance to be positioned in the vicinity of the magnetic field generator at a region where the magnetic field generated by the magnetic field generator is capable of being applied to the magnetically responsive substance such that a preset color or light transmittance is indicated along a preset pattern,
    wherein the cap is configured not to indicate the preset color or the light transmittance along the preset pattern when the movable part or the magnetic field generator is rotated along the route provided on the cap such that the magnetically responsive substance is not positioned in the vicinity of the magnetic field generator at a region where the magnetic field generated by the magnetic field generator is capable of being applied to the magnetically responsive substance.

2. The counterfeit and alteration prevention apparatus of claim 1, wherein the magnetically responsive substance is set to reflect light having a preset wavelength or transmit light at a preset transmittance as the magnetic field is applied thereto.

3. The counterfeit and alteration prevention apparatus of claim 1, wherein the magnetically responsive substance includes a solution in which magnetic particles are dispersed, and intervals between or positions of the magnetic particles are changed according to a change of the magnetic field applied thereto.

4. The counterfeit and alteration prevention apparatus of claim 1, wherein the magnetically responsive substance includes at least one of a fluorescent material, a phosphorescent material, a quantum dot material, a temperature indicating material, and an optically variable pigment (OVP) material.

5. The counterfeit and alteration prevention apparatus of claim 1, wherein the magnetically responsive substance is encapsulated into a capsule made of a light-transmissive material.

6. The counterfeit and alteration prevention apparatus of claim 1, further comprising an additional counterfeit and alteration prevention means using at least one of hologram, radio frequency identification (RFID) and biometric information recognition.

7. The counterfeit and alteration prevention apparatus of claim 1 wherein the magnetically responsive substance and the magnetic field generator are configured to be radially aligned and circumferentially overlapping when the movable part or magnetic field generator is rotated such that the preset color or light transmittance is indicated along the preset pattern, and wherein the magnetically responsive substance and the magnetic field generator are configured to be radially misaligned and circumferentially spaced from each other when the movable part or magnetic field generator is rotated such that the preset color or light transmittance is not indicated along the preset pattern.

8. A counterfeit and alteration prevention apparatus comprising:
 a magnetically responsive substance container to contain a magnetically responsive substance in which a reflected light or a transmitted light is changed when a magnetic field applied thereto is changed;
 a magnetic field generator to generate a magnetic field capable of being applied to the magnetically responsive substance; and
 a movable part to perform a function of changing an indication state of the magnetically responsive substance,
 wherein the movable part is rotated along a route provided on a cap in response to a given external stimulus to change at least one of an intensity, a direction and a pattern of the magnetic field generated by the magnetic field generator and applied to the magnetically responsive substance,
 wherein the cap is configured to indicate a preset color or light transmittance along a preset pattern when the movable part or the magnetic field generator is rotated along the route to cause the magnetically responsive substance to be positioned in the vicinity of the magnetic field generator at a region where the magnetic field generated by the magnetic field generator is capable of being applied to the magnetically responsive substance,
 wherein the cap is configured not to indicate the preset color or the light transmittance along the preset pattern when the movable part or the magnetic field generator is rotated along the route provided on the cap such that the magnetically responsive substance is not positioned in the vicinity of the magnetic field generator at a region where the magnetic field generated by the magnetic field generator is capable of being applied to the magnetically responsive substance.

9. The counterfeit and alteration prevention apparatus of claim 8, wherein the magnetically responsive substance container is disposed along a circumference of the movable part.

10. A counterfeit and alteration prevention apparatus comprising:
 a magnetically responsive substance container to contain a magnetically responsive substance which changes a reflected light or a transmitted light when a magnetic field applied thereto is changed;
 a magnetic field generator to generate a magnetic field capable of being applied to the magnetically responsive substance; and
 a movable part to perform a function of changing an indication state of the magnetically responsive substance,
 wherein the magnetically responsive substance container is disposed along a circumference of the movable part,
 wherein, the movable part or the magnetic field generator is configured to allow the movable part or the magnetic field generator to be rotated along a route provided on a cap to cause the magnetically responsive substance to be positioned in the vicinity of the magnetic field generator at a region where the magnetic field generated by the magnetic field generator is capable of being applied to the magnetically responsive substance such that a preset color or light transmittance is indicated along a preset pattern,
 wherein the cap is configured not to indicate the preset color or the light transmittance along the preset pattern when the movable part or the magnetic field generator is rotated along the route provided on the cap such that the magnetically responsive substance is not positioned in the vicinity of the magnetic field generator at a region where the magnetic field generated by the magnetic field generator is capable of being applied to the magnetically responsive substance.

11. The counterfeit and alteration prevention apparatus of claim 10, wherein the movable part rotates in response to the given external stimulus to change at least one of the intensity, direction and pattern of the magnetic field generated by the magnetic field generator and applied to the magnetically responsive substance.

12. The counterfeit and alteration prevention apparatus of claim 11, wherein the movable part rotates in response to the given external stimulus to move the magnetically responsive substance contained in the magnetically responsive substance container to the region where the magnetic field generated by the magnetic field generator is applied.

13. The counterfeit and alteration prevention apparatus of claim 11, wherein the movable part rotates in response to the given external stimulus to move the magnetic field generator to the region where the magnetic field is capable of being applied to the magnetically responsive substance.

14. The counterfeit and alteration prevention apparatus of claim 11, wherein the movable part rotates in response to the given external stimulus to move the magnetically responsive substance container to the region where the magnetic field generated by the magnetic field generator is applied.

15. The counterfeit and alteration prevention apparatus of claim 10, wherein the magnetically responsive substance reflects light having a preset wavelength or transmits light at a preset transmittance as the magnetic field is applied thereto.

16. The counterfeit and alteration prevention apparatus of claim 10, wherein at least one of the magnetically responsive substance container, the magnetic field generator and the movable part is configured in the form of at least one of a container plug, a tag, a card, a film, and a sticker.

17. The counterfeit and alteration prevention apparatus of claim 10, wherein the magnetically responsive substance includes a solution in which magnetic particles are dispersed, and a change of the magnetic field applied to the magnetic particles changes intervals between or positions of the magnetic particles.

18. The counterfeit and alteration prevention apparatus of claim 10, wherein the magnetically responsive substance includes at least one of a fluorescent material, a phosphorescent material, a quantum dot material, a temperature indicating material, and an optically variable pigment (OVP) material.

19. The counterfeit and alteration prevention apparatus of claim 10, wherein the magnetically responsive substance is encapsulated into a capsule made of a light-transmissive material.

20. The counterfeit and alteration prevention apparatus of claim 10, further comprising an additional counterfeit and alteration prevention means using at least one of hologram, radio frequency identification (RFID) and biometric information recognition.

* * * * *